US00PP27367P3

(12) United States Plant Patent
Gradziel et al.

(10) Patent No.: US PP27,367 P3
(45) Date of Patent: Nov. 15, 2016

(54) ALMOND TREE NAMED 'KESTER'

(50) Latin Name: *Prunus dulcis*
Varietal Denomination: Kester

(71) Applicant: The Regents of the University of California, Oakland, CA (US)

(72) Inventors: Thomas Gradziel, Davis, CA (US); Mario Viveros, Bakersfield, CA (US); Dale Kester, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 338 days.

(21) Appl. No.: 13/999,776

(22) Filed: Mar. 19, 2014

(65) Prior Publication Data

US 2015/0271964 P1 Sep. 24, 2015

(51) Int. Cl.
*A01H 5/08* (2006.01)

(52) U.S. Cl.
USPC ..... Plt./155

(58) Field of Classification Search
USPC ..... Plt./155
CPC ..... A01H 5/0216
See application file for complete search history.

(56) References Cited

PUBLICATIONS

The Mar. 12, 1992 Agreement for Testing Plant Varieties (No. 93-5001) between Burchell Nursery and The Regents of The University of California, 2 pages.
The Jun. 5, 1992 Agreement for Testing Plant Varieties (No. 93-5002) between Joe Van Gundy and The Regents of The University of California, 2 pages.
The Apr. 1, 1994 Agreement for Testing Plant Varieties (No. 94-5002) between Paramount Farming Co. and The Regents of The University of California, 2 pages.
The Apr. 1, 1994 Agreement for Testing Plant Varieties (No. 94-5003) between California State University, Chico and The Regents of The University of California, 2 pages.
The Apr. 1, 1994 Agreement for Testing Plant Varieties (No. 94-5004) between San Joaquin Delta College Farm and The Regents of The University of California, 2 pages.
The Feb. 12, 2004 Test Agreement for Trees (No. 2003-5088) between Fowler Nurseries, Inc. and The Regents of The University of California, 7 pages.
The Feb. 1, 2007 Test Agreement for Trees (No. 2007-5014) between The Burchell Nursery, Inc. and The Regents of The University of California, 7 pages.
The Jan. 1, 2004 Test Agreement for Trees (No. 2009-5017) between Matt Billings and The Regents of The University of California, 7 pages.
The Feb. 1, 2012 Test Agreement for Trees (No. 2012-5006) between Sierra Gold Nurseries and The Regents of The University of California, 7 pages.

*Primary Examiner* — Kent L Bell
(74) *Attorney, Agent, or Firm* — Morrison & Foerster LLP

(57) ABSTRACT

A new almond variety (*Prunus dulcis*) designated as 'Kester' is provided that is well-suited for serving as a pollenizer of the widely-grown 'Nonpareil' variety. 'Kester' is cross-compatible with 'Nonpareil' and has good bloom overlap with this variety, making 'Kester' highly complementary to 'Nonpareil' in production systems. 'Kester' has demonstrated low potential for Noninfectious Bud Failure and other serious afflictions of almond. Further, 'Kester' displays desirable tree and nut qualities, along with exceptional yields.

3 Drawing Sheets

Latin name: Botanical/commercial classification: *Prunus dulcis* new almond cultivar.

Varietal denomination: The varietal denomination of the claimed almond variety is 'Kester'.

BACKGROUND OF THE INVENTION

A major objective of almond breeding programs is the development of new varieties capable of acting as a pollenizer variety. In particular, there is a need for the development of new varieties capable of acting as a pollenizer variety for the California almond variety 'Nonpareil' (non-patented in the United States). Because of its high market quality, 'Nonpareil' has become the leading California almond variety, presently occupying approximately 40% of total almond acreage.

'Nonpareil', like most commercial almond varieties, is self-sterile and requires pollen from cross-compatible varieties for successful seed set. California almond variety 'Winters' (U.S. Plant Pat. No. 13,286) was released in 2002 as an early-Nonpareil bloom pollenizer to complement well-established late-bloom pollenizers. The California almond cultivar 'Carmel' (U.S. Plant Pat. No. 2,641) is currently the second most widely planted cultivar, currently accounting for approximately 10% of total almond production. However, the increasing incidence of the genetic disorder Noninfectious Bud Failure in the 'Carmel' variety has resulted in a dramatic decrease in new plantings of this cultivar and prompted the search for new pollenizer varieties having good kernel quality, productivity, and good overlap with the later 'Nonpareil' bloom. The new almond variety 'Kester' as described herein is a product of this breeding effort.

SUMMARY OF THE INVENTION

The present disclosure relates to a new and distinct almond cultivar (*Prunus dulcis*) that has been denominated as 'Kester' and more particularly to such an almond variety that is a cross-compatible pollenizer for the later bloom of the major California almond cv. 'Nonpareil'. In long-term regional testing, 'Kester' has demonstrated low potential for Noninfectious Bud Failure and other serious afflictions of almond, as well as demonstrating high yields of 'Nonpareil'-type kernels, maturing just after 'Nonpareil' and so is highly complementary to 'Nonpareil' in production systems.

Almond variety 'Kester' was originally identified as selection '2-19E' and was isolated from a seedling population obtained from a cross between 'Tardy-Nonpareil' and 'Arbuckle' almond varieties. Based on its promising performance, particularly its consistent bloom overlap with the later bloom of 'Nonpareil', its cross compatibility with 'Nonpareil', and its desirable tree and nut qualities, and exceptional yields, selection '2-19E' was selected as a candidate for release as the variety 'Kester'.

BRIEF DESCRIPTION OF THE TABLES

TABLE 1 shows the performance results of a Regional Variety Trial of selection '2-19E' ('Kester') relative to 'Carmel' (a standard 'Nonpareil' pollenizer) from Year 18 to Year 27.

TABLE 2 shows the performance results of a Variety Trial of selection '2-19E' ('Kester') compared with the 'Nonpareil' as the quality/productivity standard and other candidate 'Nonpareil' pollenizers from Year 29 to Year 35. In each column, values with the same letter are not significantly different ($P \leq 0.05$).

BRIEF DESCRIPTION OF THE DRAWINGS

FIG. 3A illustrates the flowering of selection '2-19E'. FIG. 3B illustrates the cropping branch of selection '2-19E'.

FIG. 4A and FIG. 4B illustrate different views of the kernels and the nuts of selection '2-19E'.

DETAILED DESCRIPTION OF THE INVENTION

Figure 1:
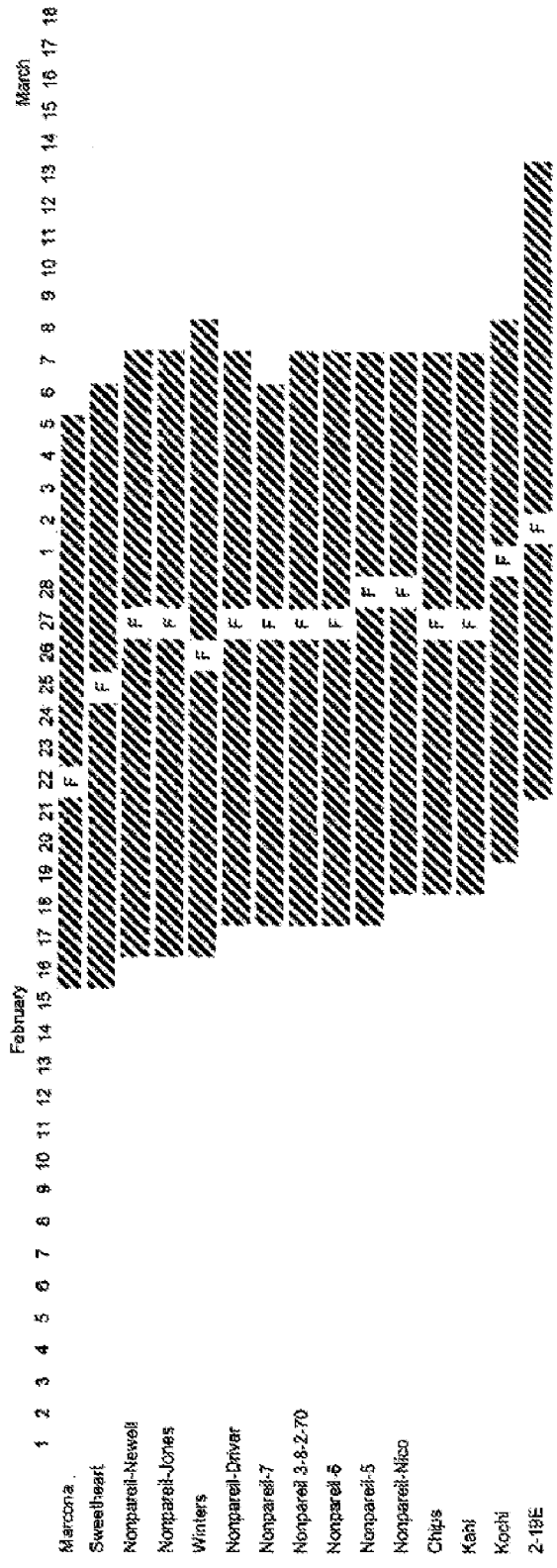
FIG. 1 illustrates the average bloom data for selection '2-19E' and other almond varieties obtained from the McFarland Trial from Year 29 to Year 34. The cross-hatched area indicates the onset of bloom to 100% petal fall. The "F" indicates full bloom. The month and the day are indicated at the top of the figure.

The original almond seedling population from which almond variety 'Kester' was selected was produced by routine crosses made during or prior to Year 1 between 'Tardy-Nonpareil', a late blooming mutation of 'Nonpareil', as the seed (female) parent and 'Arbuckle' as the pollen (male) parent. The crosses were made as part of the Calif. Expt. Stat. Proj. 739-Almond Breeding Project.

'Kester', which was evaluated under the individual seedling designation number '2-19E', was selected in Year 11 based on its desirable kernel and bloom qualities and was propagated in replicated trials in Field 7 near Winters, Calif. for further evaluation under Project POM-5884-H: Genetic Improvement of Peach and Almond. Based on its promising characteristics, selection '2-19E' was submitted in Year 14 for inclusion into the Foundation Block where it was designated by the Accession Number 03-059-01-91. In Year 15, selection '2-19E' was included in the Regional Variety Trials and grown under semi-commercial conditions. These trials were supported by California growers, which included plots in Kern County, Butte County (Chico), and San Joaquin County (Delta). Twenty-six trees each of multiple selections and varieties were included in each plot. Data of yield, phenological observations, and tree and nut characteristics have been obtained annually during Year 18 to Year 27 (TABLE 1). A record of the data obtained from these field trials is found in annual reports made to industry representatives beginning in Year 18.

In the trials shown in TABLE 1, although selection '2-19E' demonstrated good productivity and desirable tree and kernel characteristics compared to the 'Carmel' standard, performance at the Butte and San Joaquin County sites was less promising. In addition, all sites showed evidence of alternate bearing, where a high crop in one year would often be followed by a considerably lower crop the following year. Without wishing to be bound by theory, both the alternate-bearing and the lower productivity in the more northern regional variety trials are thought to be the result of insufficient agronomic inputs for an inherently highly productive selection. Accordingly, a new, replicated, test planting using semi-commercial conditions was established in McFarland, Calif. along with other candidate late-Nonpareil-bloom pollenizers during Years 29-35. The results of these trials are presented in TABLE 2. Average bloom data from these trials for selection '2-19E' and other almond varieties is presented in FIG. 1, and average hullsplitting progression data is presented in FIG. 2.

Under these improved orchard management conditions, selection '2-19E' continued to demonstrate desirable tree and kernel characteristics and good bloom overlap with the later 'Nonpareil' bloom (FIG. 1) while also demonstrating exceptional productivity without evidence for pronounced alternate bearing (TABLE 2). The high similarities between 'Nonpareil' and '2-19E' kernels may allow their mixing and may thus increase '2-19E' crop value, while the harvest time just after 'Nonpareil' allows for concurrent and even simultaneous harvest.

BOTANICAL DESCRIPTION OF THE PLANT

The following is a detailed horticultural description of the new almond variety 'Kester' obtained from vegetatively propagated progeny observed during the Year 35 and Year 36 growing seasons. The trees were vegetatively propagated by T-bud propagation onto 'Lovell' peach rootstock. The trees were grown at Foundation Plant Service Foundation Stock orchards in Davis, Calif. The younger trees for this description were $4^{th}$ leaf (4 years in the field after nursery propagation), while the older trees were $14^{th}$ leaf. Color designations are presented with reference to the "Dictionary of Color" by Maerz and Paul, First Edition (1930). All descriptions relate to those observed under early summer growth conditions, with the exception of the bloom and harvested crop descriptions. Bloom and crop performance are summarized from 6 to 12 year regional trials in Butte, Yolo, San Joaquin and Kern counties.

Botanical classification: *Prunus dulcis*, cv. 'Kester'.

'Kester' is very similar to 'Nonpareil' and its seed parent 'Tardy-Nonpareil', which is a bud-sport of 'Nonpareil', in terms of kernel quality. 'Kester' flowers approximately 3 days earlier than 'Tardy-Nonpareil' and 3 days later than 'Nonpareil', and harvests approximately 10 days after 'Nonpareil' and 5 days after 'Tardy-Nonpareil'. 'Kester' has a smaller tree size when compared to 'Nonpareil' and 'Tardy-Nonpareil', but has comparable production to 'Nonpareil' and much higher production than 'Tardy-Nonpareil'. 'Kester' possesses much better kernel quality and much higher yield than its pollen parent 'Arbuckle', which is no longer commercially planted.

Tree: The tree size is medium. When compared with the 'Nonpareil' variety, the present almond tree is smaller. The shape of the tree is upright to spreading. Tree density may be considered open and the trees exhibit moderate vigor. Generally, the trees exhibit regular bearing and bearing occurs predominantly from spurs which are two years old or older. The trees may tend to alternate-bear after years of very heavy crop. Typical $10^{th}$ leaf 'Nonpareil' tree canopies in Kern County regional grower trials were approximately 16 ft. in diameter by 17 ft. in height, while adjacent 'Kester' trees were approximately 16 ft. in diameter by 14 ft. in height.

Trunk: With regard to the tree trunk, the trunk form is generally medium as compared with other almond cultivars. The surface texture of the trunk bark for a 10 year old tree is rough with flint-gray (56-C-1) color, narrow forking fissures, and smoother, silver-gray (5-A-1) ridges having 1-2 cm lenticel scars. Typical $10^{th}$ leaf 'Kester' trunk diameters in Kern County regional grower trials were approximately 162.6 mm at 0.3 m above ground while adjacent 'Nonpareil' trees were approximately 182.9 mm at 0.3 m above ground. There are approximately 4-10 lenticels per square cm on 'Kester' scaffold wood, which is similar to 'Nonpareil' and typical for commercial almond.

Branches: The branches are average as compared with other common almond cultivars. There are relatively few tertiary branches, the present almond tree being similar to 'Nonpareil' in this aspect. The shoot surface texture is relatively slender and smooth. Shoot color is medium verdant (20-K-4) with occasional reddish flush (7-J-1). Lenticels are medium in number and small, having an orange-tan color (12-J-10).

The shoot form is straight, and has current year laterals typically at the mid to basal-section of longer shoots. Branch length is approximately 10 cm to about 30 cm, and there are approximately 10 to about 30 nodes present depending upon branch length. The branch internodes are approximately 1 to 2 cm in length. 'Kester' branch diameter is 4-7 mm at the terminal end of 1 year old shoot growth, which is typical for commercial almond.

Lateral buds are conical in shape, pointed, and develop dark brown scales (8-J-7) by late summer. Double buds may be common at a node. Two to five lateral buds will normally be found, and these will eventually become flower buds. Terminal buds are short, have a pointed shape, and are approximately 2.5 mm in diameter and 2.5 mm in length. They are small and dark (8-J-8). Lateral buds appear rounded, have a lighter brown color (8-J-12), and are approximately 1.3 mm in diameter and 1.3 mm in length, although this color and size is not distinctive. Scales are generally dark brown (8-J-7) in late summer, and non-distinctive. Spurs are generally numerous, short, and stubby. The length is approximately 1 cm. On spurs which are one year old, the epidermis takes on a green color (20-K-5), but older spurs are much darker, being a gray-brown (8-C-7).

Two year old wood generally appears somewhat stag brown (14-E-7). Three year old wood generally has many persistent peduncles and from which fruit has been borne on previous years. The color is cinnamon brown (14-H-9). Four year old wood generally shows a dull mustang brown (15-E-8) color which is evident where the epidermis has sloughed off, although this color is not particularly distinctive. Some spurs continue to produce, but many spurs are clusters of persistent peduncles from earlier production.

Leaves: The leaf quantity is abundant. Leaf shape may be considered lanceolate, occasionally elliptical, and tapering to the apex about ⅓ of the way from the apex. The leaf tip has an acuminate shape, and tapering to a more or less acute angle. The leaf base angle is rounded to oblique. The leaves have an average length of approximately 30 to 90 mm and a width of approximately 15 to about 25 mm. Leaf petioles are medium in both length and thickness. The approximate petiole length is 25 mm and the approximate petiole diameter is 1.3 mm at the base of the fully expanded leaf, which is similar to 'Nonpareil' and is typical for commercial almond. The ratio of petiole length to leaf length is approximately 0.28. The ratio of blade width to blade length is approximately 0.30.

Shoot leaves are generally medium in size, flat and substantially uniform. The color on the top surface of shoot leaves is fir green (24-L-5). The color on the bottom surface of shoot leaves is garland green (22-F-5). Leaf margins are crenate with rather shallow crenations. Leaves exhibit venation that is pinnately net veined. With regard to glands, there are usually two glands, alternate on petiole, primarily at the base of the leaf. Glands are small and have a globose form, as well as a russet green color (20-K-1) and tend to slough off with leaf age.

Figure 3:
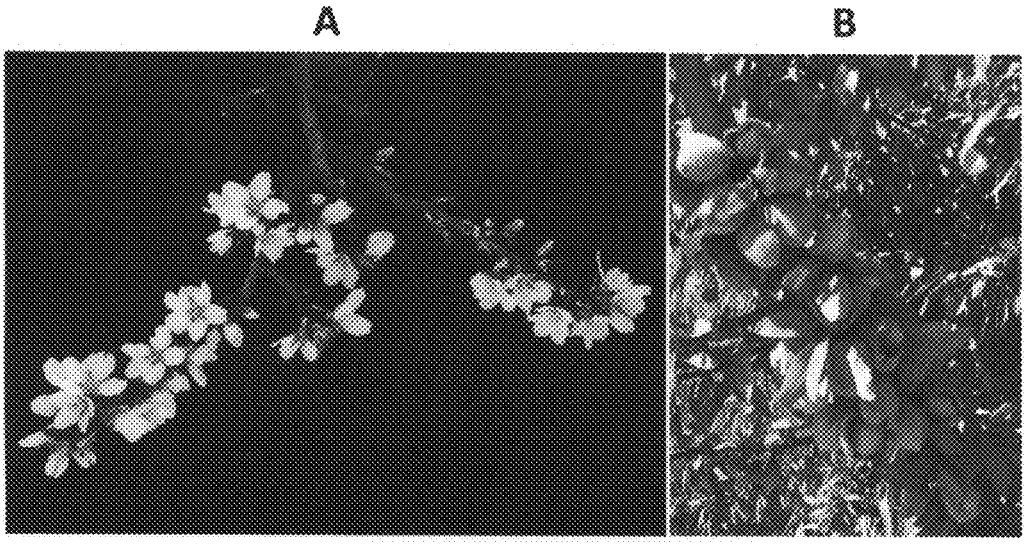
FIG. 3 illustrates various morphological phenotypes of selection '2-19E' trees.

Bloom: The amount of bloom is heavy. The bloom color is white (2-B-1) with light rose (2-J-3) developing at the petal claw. The blooming period typically starts 3-4 days after 'Nonpareil', with full bloom typically occurring 3-5 days after 'Nonpareil' full bloom. Average bloom data for the present almond variety, along with that of other almond varieties, is illustrated in FIG. 1. Historically, at the Kern County Regional Variety Trials, the average bloom period for 'Kester' is February 18 to March 5, and typical full bloom occurs around February 22. The shape of the petal apex is often retuse, occasionally with 1 to 3 shallow clefts on a rounded apex. The petal base forms a broadly cuneate, tapering claw. The configuration of the petal margin is rounded, smooth and slightly crenate at the apex. Petals have a soft velvety texture with cupping at the margins. The majority of flowers contain 5 petals. Typically, less than 3% of the flowers may contain 4 petals or 6 or more petals. The petal size is typically 14 to 20 mm long and 10 to 15 mm wide. The flower size is typically 30 to 40 mm in diameter. FIG. 3A provides an illustration of the flowers of the present variety.

Sepals are roughly triangular and are approximately 5-7 mm in length and 3-5 mm in diameter, which is similar to 'Nonpareil' and typical of commercial almond. Sepal margins are smooth and the sepal apex is conic. Sepal outer color is light green (18-G-6) and inner color is yellow green (18-F-5), although this color and size is not distinctive.

Pedicels are approximately 4.0 mm in length and 1.4 mm in diameter, which is similar to 'Nonpareil' and typical of commercial almond. Pedicel color is (18-H-6), although this color is not distinctive.

Pistil are pubescent basally over the orbicular ovary, and much less so near the stigma and upper style area. The length commonly is approximately 10 to 17 mm, including the ovary. The coloration is typically pale green (17-G-2). Pistil number is almost always 1, though 2 may rarely form.

Stamens are variable in length and commonly range from approximately 12 to 19 mm in length. They frequently extend above the pistil. The filaments are pale green (17-D-2) when young and become pale pink (1-B-1), particularly at their base, with advancing maturity. The average stamen number is 25-35.

The pollen is cross-compatible with 'Nonpareil' and so is capable of acting as a pollenizer for this cultivar. The pollen is abundant and yellow-gold (10-L-1) in coloration.

Crop: The present almond tree is a regular bearer, mostly on spurs, and has heavy productivity, with kernel yield being approximately 23.5 pounds/tree, or 2,856 pounds/acre. Nuts are well-distributed on the tree and on all sizes of wood. The harvest period is early, typically 4 to 7 days after 'Nonpareil'. At the Kern County Regional Variety Trials, the average harvest time for 'Kester' was August $2^{nd}$, one week after 'Nonpareil', which averaged July $27^{th}$. The nuts hang well on the tree yet are easy to harvest and easy to hull. FIG. 3B provides an illustration of a cropping branch of the present variety.

Immature Fruit: The side view of immature fruit is uniformly elongate, oval. The dorsal edge is slightly curved with more pronounced curving at the apical and basal ends. The ventral edge is uniformly curving along the entire length. The basal end is flat at about 75° to long axis. The apical end has a small, short acute protruding tip. The dorsal view is somewhat rugose, with slight to noticeable asymmetry between sides, particularly for larger fruit. There is a slight ridge, but is barely conspicuous. The ventral view is similar to the dorsal, but slightly less rugose and with a depressed ventral line. The apical end view is rounded with a distinct ventral ridge. The basal view is rounded, with a distinct suture line and often noticeable dorsal and ventral ridges. The base scar is round to oval and has a medium size, and also detaches cleanly. Dehiscence starts at the ventral edge, but eventually extends into the dorsal edge. Pubescence is whitish, very fine, and uniform.

Figure 2:
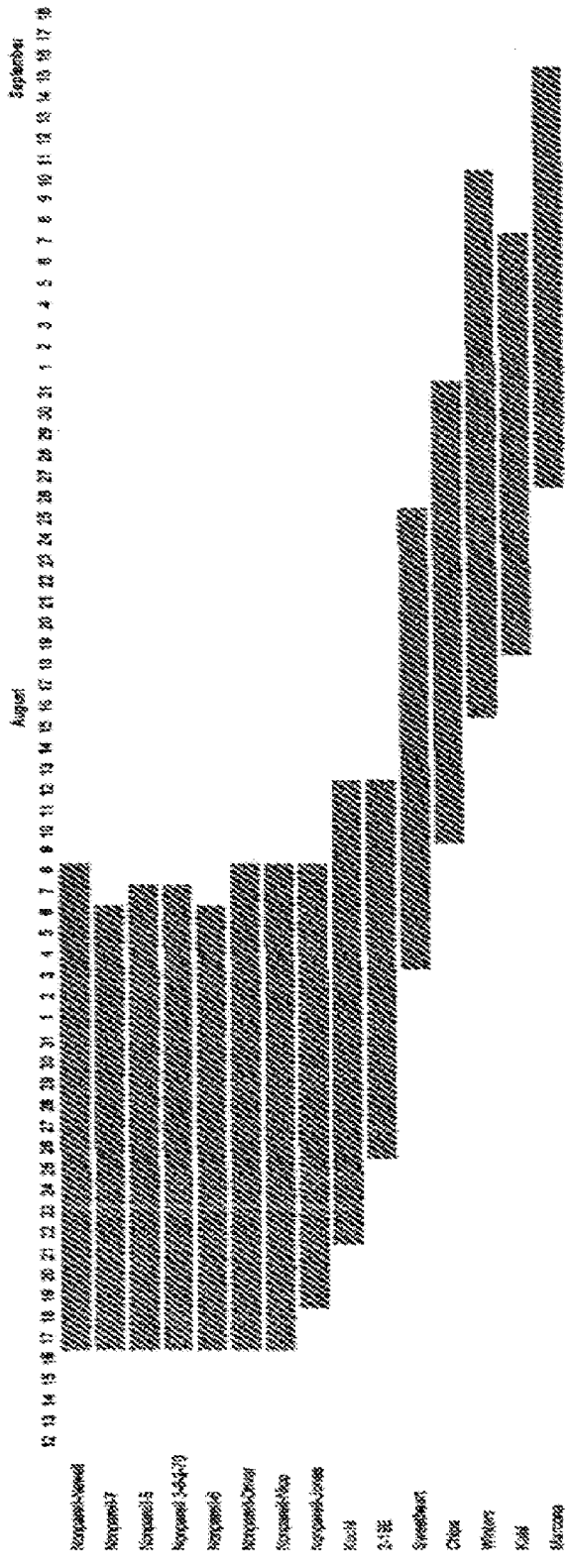
FIG. 2 illustrates the average hullsplit progression data for selection '2-19E' and other almond varieties obtained from the McFarland Trial from Year 29 to Year 34. The month and the day are indicated at the top of the figure.

Hull: The outer surface is somewhat rugose and pubescent. The form is uniform and somewhat asymmetrical as with the immature fruit. The longitudinal section form is oval. The thickness is generally 2 to 3 mm when dry. The flesh is tough but brittle when dry. The suture is medium and the color is fern green (21-I-7). In terms of dehiscence, the hull opens freely and splitting occurs along the suture. The nut cavity is oval and in terms of adherence, hulls are easily removed from nuts by mechanical hullers. Hullsplit progression in the present almond variety, along with that of other almond varieties, is illustrated in FIG. 2.

Figure 4:
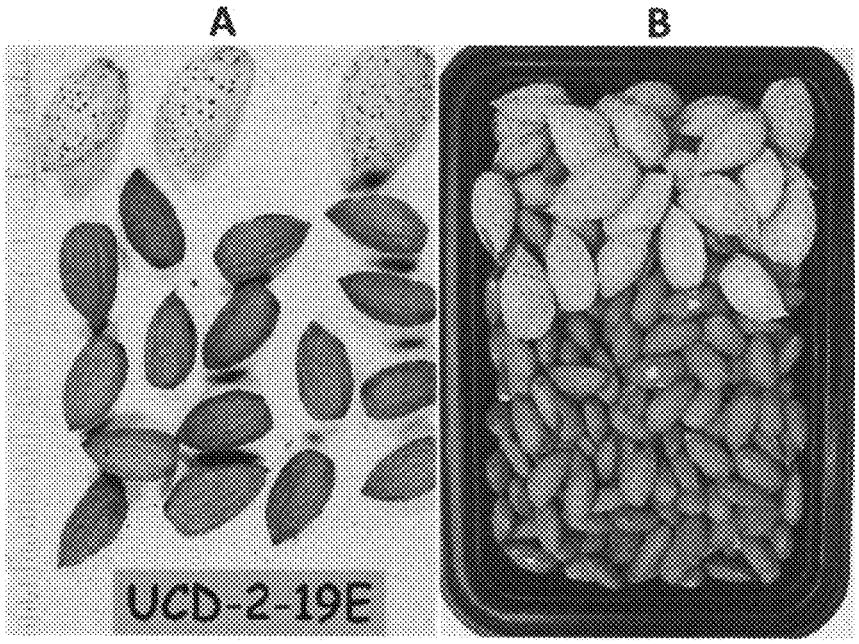
FIG. 4 illustrates various morphological phenotypes of selection '2-19E' kernel and nut. Both

Nut: The nut size is medium to large, with average dimensions of 30.5 mm in length, 22.9 mm in diameter, and 12.7 mm in thickness, being similar to 'Nonpareil'. Nuts have a medium light brown color (12-H-10). In terms of form, the length/width is elongated and the width/thickness is medium, similar to 'Nonpareil'. The shell is a paper-type and is easily cracked. There are few pits, but they are large, deep, and round. The base is ventrally oblique. The stem scar is medium, round to ovate. The apex is blunt, falcate. The wing is broad and thin, and is tapered toward the base. The inner surface is medium brown (12-I-8) and the ventral streak is narrow and lighter brown (12-H-8) in color. The percentage of kernel to nut is approximately 66%. FIG. 4A and FIG. 4B provide an illustration of the nuts and the kernels of the present variety.

Kernel: The kernel size is similar to 'Nonpareil', although slightly smaller. The average kernel length is 21 mm and the average kernel width is 11.5 mm. The average thickness is 7.8 mm and the average weight is 0.94 g. In terms of form, the length/width is medium and the width/thickness is flat, similar to 'Nonpareil'. The base is ventrally oblique and the stem scar is large, being oval to obtuse. The apex is acuminate, the texture is slightly wrinkled, the pellicle is medium, the pubescence is smooth and veined, the color is a light sayal brown (13-G-9), and the number of doubles is low, typically being less than 10%. Kernel flavor is sweet, being similar to 'Nonpareil', the quality is good, and they are readily blanchable. Kernel keeping and shipping quality are also similar to 'Nonpareil', though kernel pellicle color in 'Kester' will become slightly more brown in color with storage of several months.

Cultural characteristics: The resistance to insects of the present almond variety is comparable to that of 'Nonpareil'. The susceptibility to Noninfectious Bud Failure is low. The present variety is moderately susceptible to Hull Rot, *Alternaria* Leaf Spot, and Scab, being similar to 'Nonpareil' in this aspect.

TABLE 1

Regional Variety Trial (Year 18 to Year 27)

| | | | 2-19E | | | |
|---|---|---|---|---|---|---|
| Year | Site | Root-stock | lbs. per acre | kernel wt. in g | Crack-out (%) | Cumulative yield |
| 19 | Chico | L | 276 | 1.08 | 46.3 | 276 |
| 20 | Chico | L | 1299 | 1.01 | 51.2 | 1576 |
| 21 | Chico | L | 454 | 1.11 | 43.7 | 2029 |
| 22 | Chico | L | 1345 | 0.88 | 47.8 | 3374 |
| 23 | Chico | L | 906 | 1.13 | 46.4 | 4280 |
| 24 | Chico | L | 1828 | 0.96 | 50.8 | 6108 |
| 25 | Chico | L | 964 | 0.99 | 43.7 | 7072 |
| 26 | Chico | L | 2023 | 0.99 | 46.2 | 9095 |
| 27 | Chico | L | 1171 | 1.0 | 43.9 | 10266 |
| 19 | Delta | N | ND | ND | ND | ND |
| 20 | Delta | N | 503 | 0.97 | 55.7 | 503 |
| 21 | Delta | N | 507 | 1.02 | 50.0 | 1010 |
| 22 | Delta | N | 1010 | 1.06 | 58.2 | 2020 |
| 23 | Delta | N | 903 | 1.27 | 63.1 | 2924 |
| 24 | Delta | N | 1008 | 1.12 | 58.1 | 3932 |
| 25 | Delta | N | 1245 | 1.18 | 54.8 | 5176 |
| 26 | Delta | N | 1405 | 1.11 | 54.3 | 6581 |
| 18 | Kern | N | 341 | 1.18 | 56 | 341 |
| 19 | Kern | N | 963 | 1.17 | 47.5 | 1304 |
| 20 | Kern | N | 2347 | 0.97 | 52.7 | 3651 |
| 21 | Kern | N | 1944 | 1.07 | 52.6 | 5595 |
| 22 | Kern | N | 2496 | 0.88 | 51.2 | 8091 |
| 23 | Kern | N | 2646 | 1.17 | 60.0 | 10737 |
| 24 | Kern | N | 3479 | 1.15 | 62.1 | 14216 |
| 25 | Kern | N | 2434 | 1.01 | 56.6 | 16650 |
| 26 | Kern | N | 4890 | 1.03 | 66.5 | 21540 |
| 27 | Kern | N | 1490 | 1.1 | 48.4 | 23030 |

| | | | Carmel | | | |
|---|---|---|---|---|---|---|
| Year | Site | Root-stock | lbs. per acre | kernel wt. in g | Crack-out (%) | Cumulative yield |
| 19 | Chico | L | 741 | 1.23 | 53.2 | 844 |
| 20 | Chico | L | 1240 | 1.33 | 56.3 | 2083 |
| 21 | Chico | L | 1260 | 1.86 | 54.5 | 3343 |
| 22 | Chico | L | 1700 | 1.20 | 56.6 | 5044 |
| 23 | Chico | L | 1934 | 1.37 | ND | 6977 |
| 24 | Chico | L | 2070 | 1.13 | 52.4 | 9047 |
| 25 | Chico | L | 2320 | 1.06 | 50.7 | 11368 |

TABLE 1-continued

| Regional Variety Trial (Year 18 to Year 27) | | | | | | |
|---|---|---|---|---|---|---|
| 26 | Chico | L | 2330 | 1.20 | 53.4 | 13697 |
| 27 | Chico | L | 2830 | 1.1 | 53.0 | 16528 |
| 19 | Delta | N | 114 | 1.41 | 64.9 | 114 |
| 20 | Delta | N | 2111 | 1.16 | 60.9 | 2225 |
| 21 | Delta | N | 1893 | 1.24 | 61.2 | 4118 |
| 22 | Delta | N | 2695 | 1.24 | 58.5 | 6813 |
| 23 | Delta | N | 2538 | 1.27 | ND | 9351 |
| 24 | Delta | N | 2206 | 1.19 | 58.2 | 11556 |
| 25 | Delta | N | 2697 | 1.19 | 62.3 | 14253 |
| 26 | Delta | N | 1861 | 1.25 | 56.2 | 16113 |
| 18 | Kern | N | 634 | 1.496 | 66 | 634 |
| 19 | Kern | N | 1260 | 1.32 | 55.0 | 1893 |
| 20 | Kern | N | 1944 | 1.25 | 60.8 | 3837 |
| 21 | Kern | N | 1427 | 1.21 | 67.3 | 5264 |
| 22 | Kern | N | 1359 | 1.22 | 54.5 | 6623 |
| 23 | Kern | N | 2534 | 1.43 | ND | 9157 |
| 24 | Kern | N | 3819 | 1.24 | 62.6 | 12976 |
| 25 | Kern | N | 3398 | 1.03 | 59.8 | 16375 |
| 26 | Kern | N | 2651 | 1.24 | 63.2 | 19026 |
| 27 | Kern | N | 2778 | 1.1 | 58.9 | 21804 |

L-Lovell; N-Nemaguard; ND-No data

TABLE 2

| McFarland Variety Trial (Year 29 to Year 35) | | | |
|---|---|---|---|
| Variety | No. of nuts/tree | Average kernel wt. (g) | Shelling percentage |
| Year 29 | | | |
| 2-19e | 6852 a | 0.94 g | 53.0 d |
| Nonpareil-70 | 3848 bc | 1.07 cde | 64.6 ab |
| Nonpareil-J | 3717 bcd | 1.08 cde | 64.0 abc |
| Chips | 3623 bcd | 1.02 f | 53.6 d |
| Kochi | 3134 cd | 1.16 b | 59.9 c |
| Nonpareil-7 | 3268 bcd | 1.08 cde | 65.1 a |
| Kahl | 3139 cd | 1.06 ef | 47.6 e |
| Year 30 | | | |
| 2-19e | 13149 a | 0.76 e | 54.3 d |
| Nonpareil-70 | 9340 cde | 0.92 bc | 66.3 a |
| Kahl | 9594 cd | 0.91 bc | 47.6 e |
| Nonpareil-J | 9137 cde | 0.89 bcd | 65.5 a |
| Chips | 7681 defg | 0.87 cd | 54.4 d |
| Kochi | 6006 g | 1.08 a | 59.4 bc |
| Year 31 | | | |
| 2-19e | 13472 a | 0.93 g | 54.3 d |
| Nonpareil-70 | 12506 bcd | 1.17 cd | 66.3 a |
| Nonpareil-J | 11071 d | 1.09 cde | 65.5 a |
| Kahl | 10720 de | 0.96 fg | 47.6 e |
| Chips | 11465 cd | 0.97 fg | 54.4 d |
| Kochi | 5882 f | 1.28 b | 59.5 bc |
| Year 32 | | | |
| 2-19e | 14706 a | 0.84 f | 65.6 f |
| Nonpareil-70 | 13758 ab | 1.04 bcd | 74.6 ab |
| Nonpareil-J | 12803 abc | 1.04 bcd | 71.6 bcd |
| Kahl | 11035 cde | 0.87 ef | 59.1 g |
| Chips | 9771 ef | 0.93 def | 58.6 g |
| Kochi | 7252 g | 1.17 a | 68.9 de |
| Year 33 | | | |
| Nonpareil-70 | 8823 bcd | 1.26 abcd | 72.3 ab |
| 2-19e | 6833 efg | 1.10 bcdef | 56.1 e |
| Nonpareil-Jones | 8315 cde | 1.23 abcdef | 70.9 ab |
| Chips | 9089 abc | 1.15 bcdef | 65.9 abc |
| Kahl | 7587 cde | 1.01 f | 56.5 de |
| Kochi | 3902 h | 1.40 a | 64.4 bcd |
| Year 34 | | | |
| Nonpareil-70 | 17744 abc | 1.05 bc | 70.7 a |
| 2-19e | 18253 ab | 0.91 bcde | 64.6 abcd |

TABLE 2-continued

| McFarland Variety Trial (Year 29 to Year 35) | | | |
|---|---|---|---|
| Nonpareil-Jones | 16993 abcd | 0.96 bcde | 70.0 ab |
| Chips | 11901 f | 0.94 bcde | 60.3 de |
| Kahl | 12420 f | 0.89 cde | 53.5 f |
| Kochi | 8704 g | 1.22 a | 63.5 cde |
| Year 35 | | | |
| Nonpareil-70 | 8530 b | 1.2 bc | 70.9 bc |
| 2-19e | 7617 bc | 1.19 bcd | 69.4 bcd |
| Nonpareil-Jones | 8855 b | 1.16 bcd | 67.7 bcd |
| Chips | 9008 b | 0.92 h | 75.3 ab |
| Kahl | 8830 b | 1.05 fg | 55.0 d |
| Kochi | 2025 d | 1.41 a | 26.0 e |

| Variety | Kernel pounds per Tree | Kernel pounds per Acre | Cumulative kernel yield (lbs/acre) |
|---|---|---|---|
| Year 29 | | | |
| 2-19e | 14.2 a | 1718 a | 1718 a |
| Nonpareil-70 | 9.1 bcd | 1101 bcd | 1101 bcd |
| Nonpareil-J | 8.6 bcd | 1066 bcd | 1066 bcd |
| Chips | 8.1 bcde | 985 bcde | 985 bcde |
| Kochi | 8.0 cde | 965 cde | 965 cde |
| Nonpareil-7 | 7.6 de | 941 de | 941 de |
| Kahl | 7.4 de | 889 def | 889 def |
| Year 30 | | | |
| 2-19e | 22.6 a | 2756 a | 4474 a |
| Nonpareil-70 | 18.9 abcd | 2291 abcd | 3393 b |
| Kahl | 19.3 abcd | 2332 abcd | 3222 bcd |
| Nonpareil-J | 17.8 bcde | 2152 bcde | 3218 bcd |
| Chips | 14.7 ef | 1780 ef | 2766 bcd |
| Kochi | 14.3 ef | 1729 ef | 2694 de |
| Year 31 | | | |
| 2-19e | 27.4 cd | 3321 cd | 7795 a |
| Nonpareil-70 | 30.7 b | 3714 b | 7106 bc |
| Nonpareil-J | 26.6 de | 3224 de | 6442 cd |
| Kahl | 22.6 fg | 2733 fg | 5954 de |
| Chips | 24.4 ef | 2956 ef | 5722 ef |
| Kochi | 16.5 h | 2002 h | 4698 g |
| Year 32 | | | |
| 2-19e | 27.1 c | 3285 c | 11080 a |
| Nonpareil-70 | 31.4 ab | 3798 ab | 10905 abc |
| Nonpareil-J | 29.0 bc | 3513 bc | 9955 cd |
| Kahl | 21.1 de | 2559 de | 8513 ef |
| Chips | 20.0 e | 2422 e | 8144 ef |
| Kochi | 18.7 e | 2259 e | 6955 h |
| Year 33 | | | |
| Nonpareil-70 | 24.9 a | 3011 a | 13916 ab |
| 2-19e | 18.7 bc | 2020 bc | 13100 bc |
| Nonpareil-Jones | 22.6 a | 2737 a | 12691 c |
| Chips | 23.0 a | 2789 a | 10933 d |
| Kahl | 16.9 b | 2048 c | 10561 d |
| Kochi | 12.1 bc | 1466 bc | 8421 e |
| Year 34 | | | |
| Nonpareil-70 | 41.0 a | 4962 a | 18878 ab |
| 2-19e | 36.8 a | 4460 a | 17560 cd |
| Nonpareil-Jones | 36.0 a | 4360 a | 17051 d |
| Chips | 24.7 bcd | 2985 bcd | 13918 e |
| Kahl | 24.4 bcd | 2953 bcd | 13514 e |
| Kochi | 23.3 d | 2825 d | 11247 f |
| Year 35 | | | |
| Nonpareil-70 | 22.6 ab | 2733 ab | 21611 ab |
| 2-19e | 20.1 abc | 2432 abc | 20270 bc |
| Nonpareil-Jones | 23.0 ab | 2783 ab | 19833 c |
| Chips | 16.2 bc | 2201 bc | 16416 d |
| Kahl | 20.4 abc | 2465 abc | 15979 d |
| Kochi | 6.3 d | 763 d | 12816 e |

What we claim is:

1. A new and distinct variety of almond tree designated 'Kester' as shown and described herein.

* * * * *